(12) United States Patent
Su et al.

(10) Patent No.: US 10,150,972 B2
(45) Date of Patent: Dec. 11, 2018

(54) COMPOSITION TO ENHANCE IMMUNITY

(71) Applicant: TAIWAN INDIGENA BOTANICA CO., LTD., Taipei (TW)

(72) Inventors: Ching-Hua Su, Taipei (TW); Cheng-Jeng Tai, Taipei (TW); Bao-Hong Lee, Tainan (TW); Chen-Jei Tai, Taipei (TW); Yeu-Ching Shi, New Taipei (TW)

(73) Assignee: TAIWAN INDIGENA BOTANICA CO., LTD., Taipei (TW)

( * ) Notice: Subject to any disclaimer, the term of this patent is extended or adjusted under 35 U.S.C. 154(b) by 0 days.

(21) Appl. No.: 15/384,388

(22) Filed: Dec. 20, 2016

(65) Prior Publication Data
US 2017/0335348 A1 Nov. 23, 2017

(30) Foreign Application Priority Data

May 20, 2016 (TW) .............................. 105115736 A

(51) Int. Cl.
*A61K 36/81* (2006.01)
*C12P 1/04* (2006.01)
*C12P 1/02* (2006.01)

(52) U.S. Cl.
CPC .. *C12P 1/04* (2013.01); *C12P 1/02* (2013.01)

(58) Field of Classification Search
None
See application file for complete search history.

(56) References Cited

U.S. PATENT DOCUMENTS

2005/0084547 A1* 4/2005 Subbiah ............... A61K 31/704
424/740

FOREIGN PATENT DOCUMENTS

CN 102787048 A * 11/2012
CN 103756862 A * 4/2014

OTHER PUBLICATIONS

Cong, J. et al. Nutrition Ingredient Analysis of Solanum nigrum Fermentation Liquid Under Different Conditions. Shipin Gongye Keji 35(2)158-161, 2014 (Year: 2014).*
Opande, G. et al. Antimicrobial Activities of Crude Leaf Extract of Solanum nigrum . . . J of Asian Scientific Research 7(7)271-278, 2017. (Year: 2017).*
Lin, K. et al. Processing Technology of *Solanum nigrum* L. Lactic Acid Fermentation Drink. Academic Periodical of Farm Products Processing vol. 4, pp. 32-34, Apr. 2014. (Year: 2014).*

* cited by examiner

*Primary Examiner* — Ralph J Gitomer
(74) *Attorney, Agent, or Firm* — Anova Law Group, PLLC

(57) ABSTRACT

The present invention provides a composition for enhancing immunity. Differing from all commercial vitamin healthcare foods would cause some adverse effects due to excessive vitamin intake, the present invention proposes a *Solanum nigrum*-fermented product to be a novel composition for enhancing immunity. Moreover, animal experimental results have proved that, this novel composition would not cause any adverse effects (such as poor appetite or liver damage) even if an adult excessively administer the novel composition. In addition, comparing with the commercial healthcare foods always being made to tablets, the *Solanum nigrum*-fermented product (i.e., the novel composition) can be processed to various forms, such as powder, tablet, capsule, and drink.

3 Claims, 4 Drawing Sheets

COMPOSITION TO ENHANCE IMMUNITY

BACKGROUND OF THE INVENTION

1. Field of the Invention

The present invention relates to the technology field of fermented products, and more particularly to a specific composition made by treating a *Solanum nigrum* fermented liquid with a freeze-drying process in a vacuum environment, and this specific composition is used to enhance immunity.

2. Description of the Prior Art

Immune system is a disease defense system existing in an organism. To function properly, a normal immune system is able to detect a wide variety of agents, known as pathogens, from viruses to parasitic worms, and distinguish them from the organism's own healthy tissue. Because vertebrate immune system comprises various proteins, cells, organs, and tissues, the vertebrate immune system derives a variety of immune mechanisms, including: phagocytosis, antimicrobial peptides called defensins, and complement system.

Immune system can be further divided into innate immune system and adaptive immune system, wherein the pathogens or viruses succeeding to enter organism by breaking organism's surface barriers would be identified and attacked by the innate immune system. It is well known that innate immune leukocyte includes: phagocyte (such as macrophages, neutrophils and dendritic cells), mast cells, eosinophils, basophils, and natural killer cells, wherein macrophages play a significant part in human immune system.

Although immune system expresses the characteristics of specificity, inducibility and adaptation, disorders of the immune system would take place under following three situations: hypoimmunity, autoimmune and hypersensitivity. As the person skilled in biotech fields well knows, hypoimmunity and autoimmune are resulted from the inactivation of some parts of immune system. In general, the body immunity of a man older than 50 years of age will gradually decline, so that the old people are easier to suffer with hypoimmunity than young people. However, beside the age factor, malnutrition, obesity, alcoholism, and drug abuse are also the important factors for causing people suffer with the hypoimmunity.

For the modern people living high-pressure life with unbalanced diet, it is very difficult for them to enhance immunity by absorbing enough nutrients from daily foods. So that, modern people often take complex vitamins in order to enhance their immunity. However, although commercial complex vitamin products have nutrition labeling, most of people do not know the recommended daily intake of one single vitamin or the complex vitamins, and that may cause people administer vitamins excessively so as to induce the occurrence of various adverse effects. The common adverse effects induced by the excessive vitamin intake are listed in following Table (1).

TABLE 1

| Vitamins | adverse effects resulted from excessive vitamin intake |
| --- | --- |
| Vitamin A | Dermatitus, skin irritation, headache, hepatomegaly, splenomegaly, poor appetite, and stomach upset |
| Vitamin C | Stomach inflammation, stomach upset, and diarrhea |
| Vitamin D | Calcium deposition occurs in kidney, heart, or blood vessel due to excessive calcium absorption. |
| Vitamin B1, B6 | The over-intake vitamin B1 or B6 will be exhausted with urine. |

From above descriptions, it is able to know that an adult may develop the hypoimmunity with age growing; so that, it is very important for an elderly man to enhance his immunity by taking healthcare foods. Thus, in view of most of the commercial vitamin products may induce adverse effects resulted from excessive vitamin intake, the inventor of the present application has made great efforts to make inventive research thereon and eventually provided a composition for enhancing immunity.

SUMMARY OF THE INVENTION

The primary objective of the present invention is to provide a composition for enhancing immunity. Differing from all commercial vitamin healthcare foods would cause some adverse effects due to excessive vitamin intake, the present invention proposes a *Solanum nigrum*-fermented product to be a novel composition for enhancing immunity. Moreover, animal experimental results have proved that, this novel composition would not cause any adverse effects (such as poor appetite or liver damage) even if an adult excessively administer the novel composition. In addition, comparing with the commercial healthcare foods always being made to tablets, the *Solanum nigrum*-fermented product (i.e., the novel composition) can be processed to various forms, such as powder, tablet, capsule, and drink (liquid).

In order to achieve the primary objective of the present invention, the inventor of the present invention provides an embodiment for the composition for enhancing immunity, which is a *Solanum nigrum*-fermented product; wherein a specific intake dose for an adult is helpful to enhance body immunity of the adult, and the specific intake dose is at least 2.5 gram.

In the aforesaid embodiment of the composition for enhancing immunity, the *Solanum nigrum*-fermented product is selected from the group consisting of: *Solanum nigrum*-fermented liquid, *Solanum nigrum*-fermented powder obtained by drying the aforesaid *Solanum nigrum*-fermented liquid, *Solanum nigrum*-fermented tablet obtained by processing the aforesaid *Solanum nigrum*-fermented powder, and *Solanum nigrum*-fermented capsule obtained by processing the aforesaid *Solanum nigrum*-fermented powder.

In the aforesaid embodiment of the composition for enhancing immunity, the *Solanum nigrum*-fermented product is manufactured through following a plurality of culturing steps:

step (1): applying a washing treatment to a raw material of *Solanum nigrum*, and then grinding the raw material of *Solanum nigrum* to a *Solanum nigrum* powder;

step (2): mixing and modulating the *Solanum nigrum* powder, a soybean flour, and a liquid culture medium to a culture liquid;

step (3): treating the culture liquid with a sterilizing process by using a high temperature and pressure autoclave;

step (4): inoculating a *Lactobacillus* strain and a yeast strain to the culture liquid; and step (5): treating the culture liquid obtained from the step (4) with a culturing process.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE PREFERRED EMBODIMENTS

Figure 1:
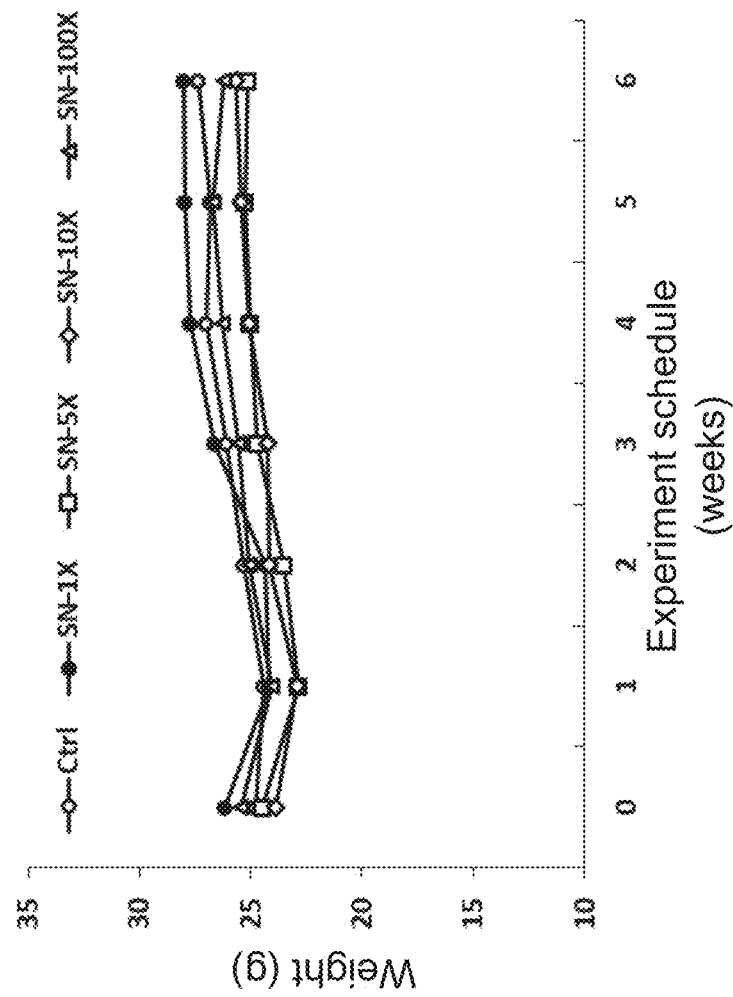
FIG. 1 shows a plot curve graph of experiment schedule versus cell weight of mice.

To more clearly describe a composition for enhancing immunity according to the present invention, embodiments of the present invention will be described in detail with reference to the attached drawings hereinafter.

*Solanum nigrum*, belonging to the family of Solanaceae plants, is found having the functionalities of detoxification, diuretic, eliminating edema, curing cough, and reducing phlegm. Moreover, researching and studying data have proved that *Solanum nigrum* also possesses some medical effects such as anti-inflammatory, anti-shock, anti-allergy, and anti-tumor. Currently, *Solanum nigrum* has been clinically applied on the curing of various cancers and liver ascites.

On the other hand, resulted from long-term administering synthetical healthcare foods may induce a variety of adverse or side effects, more and more people start to pay attention on the intake of natural healthy foods. In the present invention, a novel composition made by treating a *Solanum nigrum* fermented liquid with a vacuum freeze-drying process is proposed, and this novel composition is particularly used to enhance immunity. In briefly, this novel composition is a *Solanum nigrum* fermented product and can be manufactured through following a plurality of culturing steps.

First of all, step (1) of the plurality of culturing steps is executed for washing a raw material of *Solanum nigrum* under 44-55° C. for 24-48 hours, and then grinding the raw material of *Solanum nigrum* to a *Solanum nigrum* powder. Next, step (2) of the plurality of culturing steps is executed for mixing and modulating the *Solanum nigrum* powder, a soybean flour and a liquid culture medium to a culture liquid. In step (2), the *Solanum nigrum* powder and the liquid culture medium are mixed according to a first mixing ration in a range from 1:10 to 1:40, and the soybean flour and the liquid culture medium are mixed according to a second mixing ration in a range from 1:5 to 1:20. Moreover, following Table (1) provides an exemplarily modulation formula of the *Solanum nigrum*-fermented liquid and the liquid culture medium.

TABLE 1

| Ingredient | Content (gram per 100 mL deionized water) |
|---|---|
| Glucose | 1 |
| *Solanum nigrum* powder | 10 |

TABLE 1-continued

| Ingredient | Content (gram per 100 mL deionized water) |
|---|---|
| Soybean flour | 10 |
| Powdered *Lactobacillus* | 2 |
| Powdered yeast | 1 |
| $KH_2PO_4$ | 0.01 |
| $K_2HPO_4$ | 0.01 |
| trace vitamins | 0.005 |

Continuously, step (3) of the plurality of culturing steps is executed for treating the culture liquid with a sterilizing process by using a high temperature and pressure autoclave. Moreover, after the step (3), step (4) and step (5) are executed for inoculating a *Lactobacillus* strain and a yeast strain to the culture liquid, and then treating the culture liquid a culturing process under 25-30° C. for 3-7 days. Eventually, step (6) of the plurality of culturing steps is executed for processing the *Solanum nigrum* fermented liquid to a *Solanum nigrum* fermented product.

Herein it needs to particularly explain that, the exemplarily modulation formula and mixing ratio of the *Solanum nigrum* powder, the soybean flour and the liquid culture medium cannot be used for limiting the modulation formula when manufacturing the novel composition having functionality to enhance immunity. As the biotech engineers skilled in culture and fermentation process well know, it is very easy to modulate other formulas for making the *Solanum nigrum*-fermented liquid and the liquid culture medium like the two provided in Table (1). On the other hand, although the *Solanum nigrum*-fermented liquid is processed to a *Solanum nigrum*-fermented powder in the step (6), the *Solanum nigrum*-fermented powder is used for carrying out animal experiments, but not for limiting the final product type of the composition having functionality to enhance immunity proposed by the present invention. In practicable application, the composition can be a *Solanum nigrum*-fermented liquid, a *Solanum nigrum*-fermented powder obtained by drying the aforesaid *Solanum nigrum*-fermented liquid, a *Solanum nigrum*-fermented tablet obtained by processing the aforesaid *Solanum nigrum*-fermented powder, and a *Solanum nigrum*-fermented capsule obtained by processing the aforesaid *Solanum nigrum*-fermented powder.

In briefly, the composition for enhancing immunity of the present invention is a *Solanum nigrum*-fermented product. Moreover, a specific intake dose for an adult is helpful to enhance body immunity of the adult, wherein the specific intake dose is at least 2.5 gram. For proving the immunity enhancing effect of the *Solanum nigrum*-fermented product, an animal experiment is particularly designed and completed by the inventors of the present invention. As following Table (2) shows, C57BL/6 mice are taken as the experimental animals and divided into 5 groups, including: control (Ctrl) group, 1-fold dose (SN-1×) group, 5-fold dose (SN-5×) group, 10-fold dose (SN-10×) group, and 100-fold dose (SN-100×) group.

TABLE 2

| Group | Animal feeds |
|---|---|
| Ctrl | Rodent chow diet 5001 |
| SN-1X | Rodent chow diet 5001 + *Solanum nigrum*-fermented product of 1-fold dosage |

TABLE 2-continued

| Group | Animal feeds |
|---|---|
| SN-5X | Rodent chow diet 5001 + Solanum nigrum-fermented product of 5-fold dosage |
| SN-10X | Rodent chow diet 5001 + Solanum nigrum-fermented product of 10-fold dosage |
| SN-100X | Rodent chow diet 5001 + Solanum nigrum-fermented product of 100-fold dosage |

In the animal experiment, the conversion between adult dose and animal dose of all test samples are carried out according to the guidance of estimating the maximum safe starting dose in initial clinical trials for therapeutics in adult healthy volunteer provided by U.S. Food and Drug Administration (USFDA). An easy formula for converting the adult dose to the animal dose is presented as follows: mouse equivalent dose per kilogram=(human equivalent dose per kilogram/60 kg)×12.3. Therefore, all of the mouse equivalent doses for the groups of animal experiment are calculated and listed in following Table (3).

TABLE 3

| Group | Test sample | Mouse equivalent dose (mg/kg*bw/day) | Human equivalent dose (mg/day) |
|---|---|---|---|
| Ctrl | RO water | — | — |
| SN-1X | Powdered | 102 | 500 |
| SN-5X | Solanum | 512 | 2500 |
| SN-10X | nigrum-fermented | 1024 | 5000 |
| SN-100X | product | 10240 | 50000 |

Moreover, schedule of the animal experiment is planned as follows:
Weeks 1-3: pre-feeding the mice of the 5 groups for 3 weeks;
Weeks 4-9: feeding the mice of the 5 groups by the animal feeds listed in Table (2) along with the mouse equivalent doses listed in Table (3), for 6 weeks;
Week 9: sacrificing the mice of the 5 groups and then separating spleen cells and livers from the mice, for carrying out a phagocytosis test and making liver tissue slices, respectively.

Figure 2:
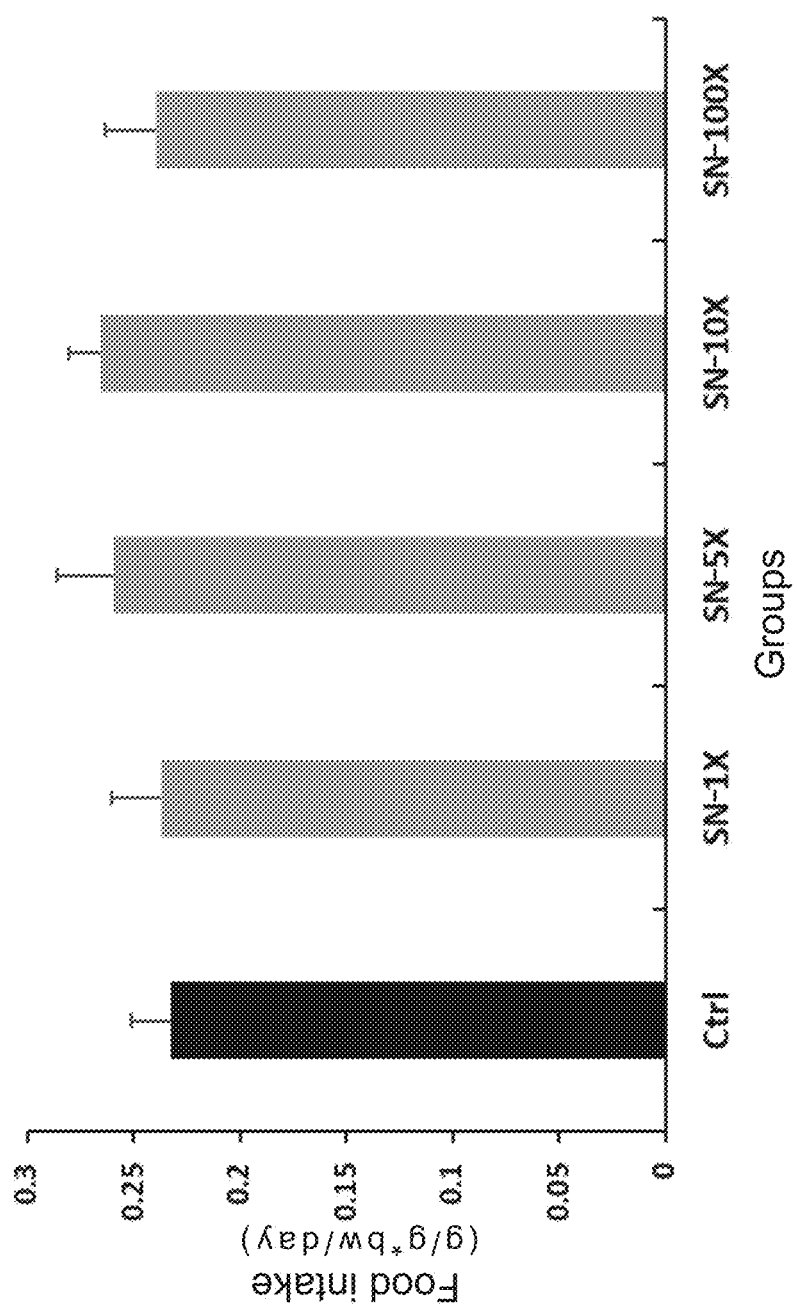
FIG. 2 shows a statistics bar chart of experimental groups versus food intake.

Please refer to FIG. 1, which shows a plot curve graph of experiment schedule versus cell weight of mice. Moreover, FIG. 2 shows a statistics bar chart of experimental groups versus food intake. From FIG. 1, it can find that the weight of the mice of the groups Ctrl and SN-1× reveals trace increase after comparing with the mice of the groups SN-5×, SN-10× and SN-100×. Moreover, it can also know that feeding the mice with high-dosage Solanum nigrum-fermented product would not induce the occurrence of any adverse effects. In briefly, the mice would not suffer with loss of appetite even if the mice have been fed with high-dosage Solanum nigrum-fermented product from a long time.

Figure 3:
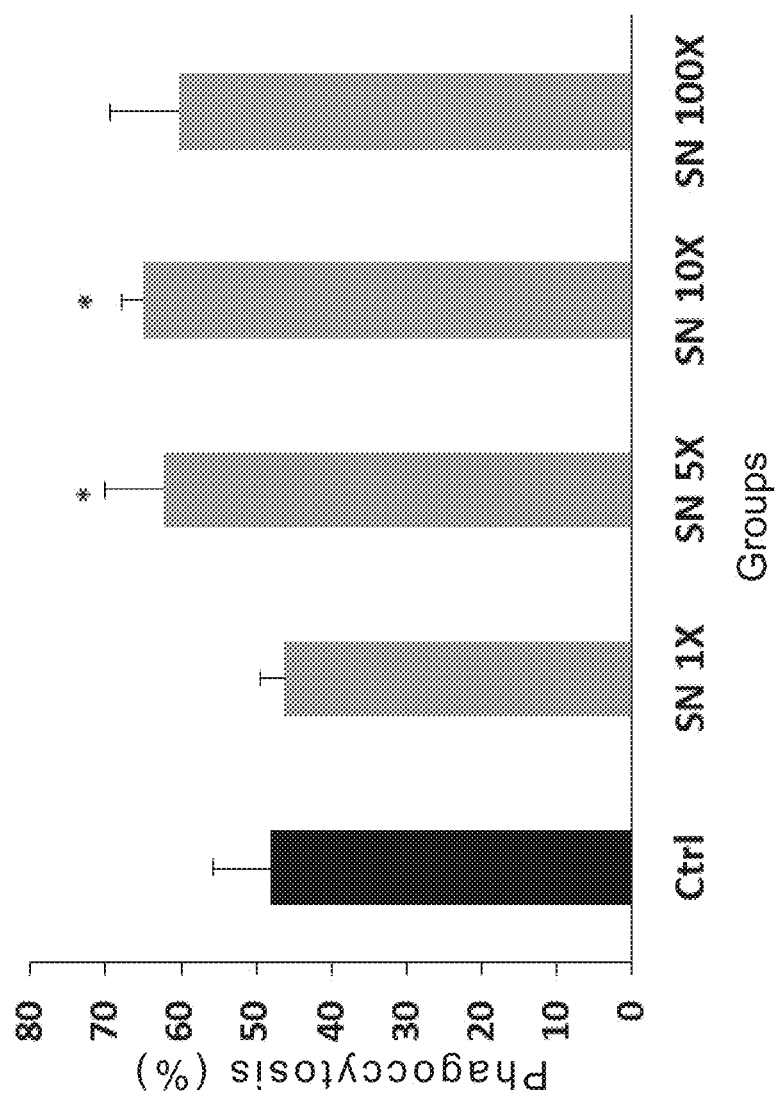
FIG. 3 shows a statistics bar chart of experimental groups versus phagocytosis.

In week 9, the spleen cells separated from the mice are washed by red blood cell lysis buffer. After that, the spleen cells of $1\times10^4$ count/mL are disposed into a plurality of test tubes of a flow cytometer. Moreover, after adding Escherichia coli with green fluorescent into the professional test tubes, a phagocytosis test is then completed by the flow cytometer. Please refer to FIG. 3, where a statistics bar chart of experimental groups versus phagocytosis is provided. From FIG. 3, it can easily find that, the spleen macrophages of the mice of the groups SN-5× and SN-10× perform stronger phagocytosis than the spleen macrophages of the mice of the group Ctrl. Moreover, compared to the group Ctrl, the phagocytosis expressed by the spleen macrophages of the mice of the groups SN-100× is more active. Therefore, the experimental data have proved that the Solanum nigrum-fermented product (i.e., the novel composition of the present invention) indeed can promote phagocytosis, so as to enhance body immunity.

Figure 4:
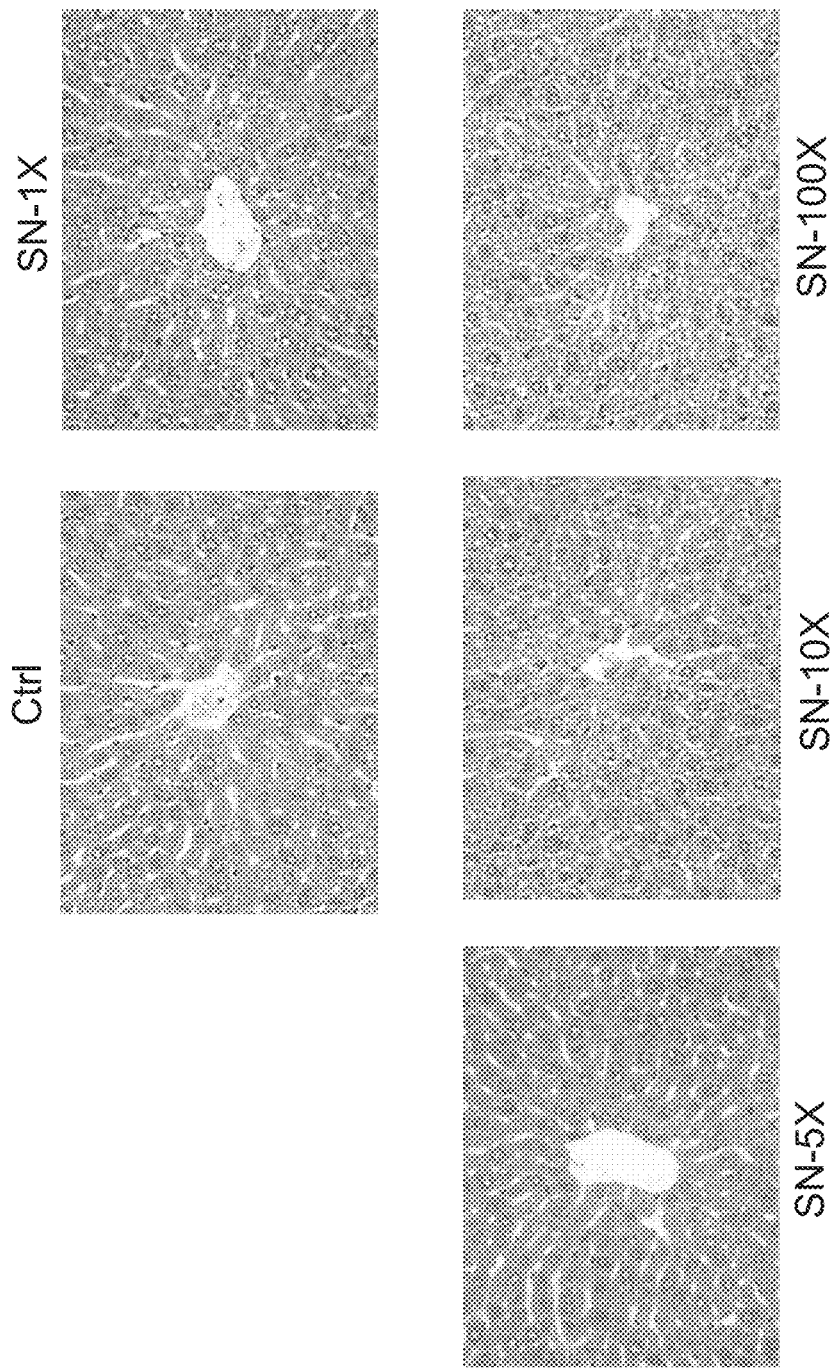
FIG. 4 shows tissue slice images of liver taken out from experimental mice.

Moreover, in week 9, the livers separated from the mice are made to liver tissue slices in order to determine whether the novel composition would induce toxicity in organism. Please refer to FIG. 4, there are shown FIG. 4 shows tissue slice images of liver taken out from experimental mice. From FIG. 4, it can find that the liver tissue is not subjected with any damages. Therefore, the liver tissue slices have proved that the mice would not suffer with any adverse effects even if the mice have been fed with high-dosage Solanum nigrum-fermented product from a long time.

Therefore, through above descriptions, the composition for enhancing immunity provided by the present invention has been introduced completely and clearly; in summary, the present invention includes the advantages of:

(1) Differing from all commercial vitamin healthcare foods would cause some adverse effects due to excessive vitamin intake, the present invention proposes a Solanum nigrum-fermented product to be a novel composition for enhancing immunity. Moreover, animal experimental results have proved that, this novel composition would not cause any adverse effects (such as poor appetite or liver damage) even if an adult excessively administer the novel composition.

(2) In addition, comparing with the commercial healthcare foods always being made to tablets, the Solanum nigrum-fermented product (i.e., the novel composition) can be processed to various forms, such as powder, tablet, capsule, and drink.

The above description is made on embodiments of the present invention. However, the embodiments are not intended to limit scope of the present invention, and all equivalent implementations or alterations within the spirit of the present invention still fall within the scope of the present invention.

What is claimed is:
1. A composition for enhancing immunity, comprising:
a culture liquid, comprising:
a liquid culture medium;
a Solanum nigrum powder mixed into the liquid culture medium; and
a soybean flour mixed into the liquid culture medium;
a Lactobacillus strain inoculated into the culture liquid; and
a yeast strain mixed into the culture liquid;
wherein the Solanum nigrum powder and the liquid culture medium have a first mixing ratio in a range from 1:10 to 1:40 by weight, and the soybean flour and the liquid culture medium have a second mixing ratio in a range from 1:5 to 1:20 by weight;
wherein the composition is a Solanum nigrum-fermented product of the culture liquid, the Lactobacillus strain, the yeast strain.
2. The composition of claim 1, wherein the Solanum nigrum-fermented product is further processed to an oral dosage form selected from the group consisting of liquid, powder, tablet, and capsule.

3. The composition of claim 1, wherein a therapeutically effective dosage of the composition for an adult is at least 2.5 grams, so as to enhance immunity by promoting phagocytosis.

* * * * *